US00PP34858P2

(12) United States Plant Patent
Provost

(10) Patent No.: US PP34,858 P2
(45) Date of Patent: Dec. 20, 2022

(54) **NEW GUINEA *IMPATIENS* PLANT NAMED 'KLENI21180'**

(50) Latin Name: *Impatiens hawkeri*
Varietal Denomination: KLENI21180

(71) Applicant: KLEMM + SOHN GMBH & CO. KG, Stuttgart (DE)

(72) Inventor: Roxane I. C. Provost, Stuttgart (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/873,922

(22) Filed: Jul. 26, 2022

(51) Int. Cl.
*A01H 6/16* (2018.01)
*A01H 5/02* (2018.01)

(52) U.S. Cl.
USPC ..... Plt./318.2

(58) Field of Classification Search
USPC ..... Plt./318.2, 318.1
See application file for complete search history.

*Primary Examiner* — Annette H Para
(74) *Attorney, Agent, or Firm* — Weatherly IP Solutions, LLC; James M. Weatherly

(57) ABSTRACT

A New Guinea *Impatiens* plant particularly distinguished by white flowers and a large flower size, is disclosed.

1 Drawing Sheet

Genus and species: *Impatiens hawkeri*.
Variety denomination: 'KLENI21180'.

BACKGROUND OF THE NEW PLANT

The present invention comprises a new and distinct variety of New Guinea *Impatiens*, botanically known as *Impatiens hawkeri*, and hereinafter referred to by the variety name 'KLENI21180'. 'KLENI21180' originated from a controlled hand-pollination between May to August 2016 in Kenya between the proprietary female New Guinea *Impatiens* variety 'KLENI17155' (unpatented) and the proprietary male New Guinea *Impatiens* variety 'NI-2015-0147' (unpatented).

The seeds from the cross were sown and plants were grown in a greenhouse for evaluation, where an individual plant designated 'KLENI21180' was selected from the group in May 2017. 'KLENI21180' was first vegetatively propagated via apical vegetative cuttings. 'KLENI21180' was found to reproduce true to type in successive generations of asexual propagation via apical vegetative cuttings.

SUMMARY

The following are the most outstanding and distinguishing characteristics of this new variety when grown under normal horticultural practices in Stuttgart, Germany.

1. White flowers; and
2. Larger flower size.

DESCRIPTION OF THE PHOTOGRAPH

This New Guinea *Impatiens* plant is illustrated by the accompanying photograph which shows the plant's overall plant habit including form, foliage, and flowers. The photograph is of a 11-week-old plant grown in a greenhouse in Stuttgart, Germany in May 2020. The colors shown are as true as can be reasonably obtained by conventional photographic procedures.

DESCRIPTION OF THE NEW VARIETY

The following detailed descriptions set forth the distinctive characteristics of 'KLENI21180'. The data which define these characteristics were collected from asexual reproductions carried out in Stuttgart, Germany. Data was collected on 20-week-old plants grown in a greenhouse in Stuttgart, Germany in April 2022. Color references are to The R.H.S. Colour Chart of The Royal Horticultural Society of London (R.H.S.), 5$^{th}$ edition (2007), unless otherwise noted.

Classification:
- *Family*.—Balsaminaceae.
- *Botanical*.—*Impatiens hawkeri*.
- *Common*.—New Guinea *Impatiens*.
- *Designation*.—'KLENI21180'.

Parentage:
- *Female parent*.—The proprietary female New Guinea *Impatiens* variety 'KLENI17155' (unpatented).
- *Male parent*.—The proprietary male New Guinea *Impatiens* variety 'NI-2015-0147' (unpatented).

Growth:
- *Propagation type*.—Vegetative, unrooted cuttings.
- *Growth habit*.—V-shaped.
- *Flowering season*.—Spring.
- *Height*.—10.0 cm.
- *Width*.—20.0 cm.
- *Time to produce a finished flowering plant*.—8 weeks.
- *Time to initiate roots*.—3 weeks.
- *Root description*.—Fibrous.
- *Rooting habit*.—Vertical and fibrous.
- *Root color*.—RHS 159C (Orange-White).

Lateral branches:
- *Quantity of stems per plant*.—9 main stems.
- *Branching habit*.—Ascending.
- *Length*.—9.0 cm.
- *Diameter*.—0.5 cm.
- *Internode length*.—3.0 cm.
- *Texture and appearance*.—Smooth and glossy.
- *Color*.—Developing (young): RHS 144B. Developed (mature): RHS 144B.

Leaves:
- *Arrangement*.—Whorled.
- *Length*.—9.0 cm.

*Width*.—4.5 cm.
*Shape*.—Lanceolate.
*Apex*.—Broad.
*Base*.—Attenuate.
*Margin*.—Serrulate.
*Texture and appearance*.—Upper surface: Smooth and glossy. Lower surface: Smooth and glossy.
*Venation pattern*.—Arcuate.
*Venation color*.—Upper surface: RHS 137C. Lower surface: RHS 187C.
*Color, developing leaves*.—Upper surface: RHS 143A. Lower surface: RHS 138B.
*Color, fully expanded leaves*.—Upper surface: RHS 139A. Lower surface: RHS 138B.
*Petiole*.—Length: 2.0 cm. Diameter: 0.4 cm. Texture and appearance (both upper and lower surfaces): Smooth and glossy. Color: Upper part: RHS 145B. Lower part: RHS 145B.

Flower:
*Flower type and habit*.—Zygomorphic, simple, pendant.
*Flower longevity*.—Flowers continuously.
*Fragrance*.—Absent.
*Natural flowering season*.—Spring.
*Diameter*.—8.0 cm.
*Depth*.—0.5 cm.

Flower buds:
*Shape*.—Ovoid when completely closed; drop shaped when partially open.
*Length*.—2.0 cm.
*Diameter*.—1.5 cm.
*Texture and appearance*.—Smooth and glossy.
*Color*.—RHS NN155B (white) and RHS 144B (green).

Petals:
*Quantity and arrangement*.—5.
*Length*.—Banner petal: 2.0 cm. Lateral petals: 3.5 cm. Lower petals: 3.0 cm.
*Width*.—Banner petal: 5.0 cm. Lateral petals: 3.5 cm. Lower petals: 4.5 cm.
*Shape, all petals*.—Cordate.
*Apex, all petals*.—Emarginate.
*Base, all petals*.—Round to acute.
*Margin all petals*.—Entire.
*Texture and appearance, all petals, both upper and lower surfaces*.—Smooth and satiny.
*Color, all petals, when opening*.—Upper surface: RHS NN155C. Lower surface: RHS NN155C.
*Color, all petals, fully opened*.—Upper surface: RHS NN155C. Lower surface: RHS NN155C.

Sepals:
*Quantity and arrangement*.—4 lateral and 1 spurred; arrangement is whorled.
*Lateral sepal*.—Length: 1.5 cm. Width: 0.7 cm. Shape: Elliptic. Apex: Caudate. Base: Rounded. Margin: Entire. Texture and appearance: Upper surface: Puberulent. Lower surface: Smooth and glossy. Color: Upper surface: RHS 145A. Lower surface: RHS 145C.
*Spurred sepal*.—Length, not including spur: 2.0 cm. Width, proximally: 1.5 cm. Shape, proximally: Obtuse. Base: Rounded. Margin, proximally: Entire. Texture and appearance, proximally: Upper surface: Pulverulent and glossy. Lower surface: Smooth and glossy. Color, proximally: Upper surface: RHS 155C. Lower surface: HRS 155C. Spur: Length: 6.5 cm. Diameter: 0.2 cm. Shape: Needle-shaped. Texture and appearance: Smooth and glossy. Color: RHS 185A.

Peduncles:
*Length*.—6.0 cm.
*Diameter*.—0.2 cm.
*Angle*.—45 degrees ascending.
*Strength*.—Moderately strong.
*Texture and appearance*.—Smooth and glossy.
*Color*.—RHS 145B.

Reproductive organs:
*Stamens*.—Quantity per flower: 5 stamens are fused and form a cap over the ovary. Filament length: Not visible. Filament color: Not visible. Anther length: 0.1 cm. Anther shape: Monothecal. Anther color: RHS 158C. Pollen color: RHS 8D. Pollen amount: Abundant.
*Pistils*.—Quantity per flower: 1. Pistil length: 0.6 cm. Stigma shape: Truncado. Stigma color: RHS 145B. Style length: 0.5 cm. Style color: RHS 143A (Green). Ovary color: RHS 145C (Yellow-Green).

Fruit and seed set: Seed set not observed to date of registration.

Disease and pest/insect resistance: No disease and pest/insect resistance observed to date.

COMPARISON WITH PARENTAL LINES AND KNOWN VARIETY

'KLENI21180' can be distinguished from its parents as described in Table 1.

TABLE 1

Comparison with Parental Lines

| Characteristic | 'KLENI21180' | Female Parent 'KLENI17155' | Male Parent 'NI-2015-0147' |
|---|---|---|---|
| Flower color | White | Lavender | Salmon Pink |

'KLENI21180' is most similar to the commercial New Guinea *Impatiens* variety 'Medina' (U.S. Plant Pat. No. 11,703). Differences between the varieties are described in Table 2.

TABLE 2

Comparison with Similar Variety

| Characteristic | 'KLENI21180' | 'Medina' |
|---|---|---|
| Flower size | Larger than 'Medina' | Smaller than 'KLENI21180' |

I claim:

1. A new and distinct variety of New Guinea *Impatiens* plant designated 'KLENI21180' as illustrated and described herein.

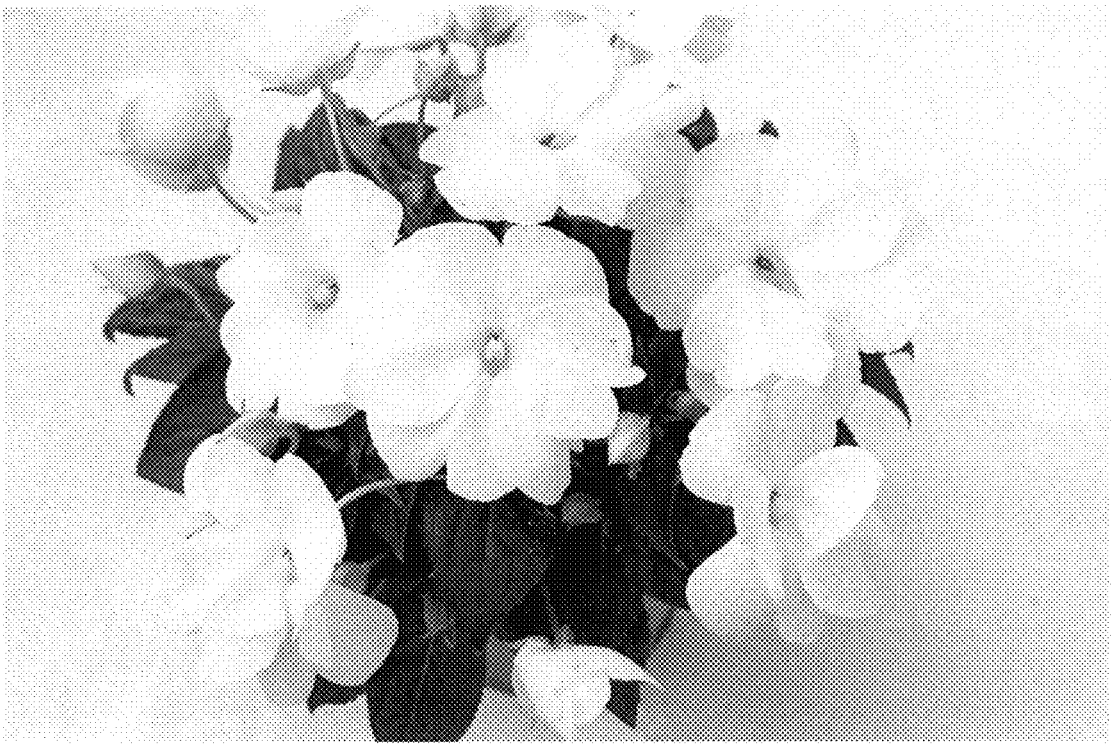

* * * * *